United States Patent
Pazenok et al.

(10) Patent No.: US 9,518,025 B2
(45) Date of Patent: Dec. 13, 2016

(54) PROCESS FOR PREPARING 3,5-BIS(HALOALKYL)PYRAZOLE DERIVATIVES FROM A,A-DIHALOAMINES

(71) Applicant: BAYER CROPSCIENCE AKTIENGESELLSCHAFT, Monheim am Rhein (DE)

(72) Inventors: Sergii Pazenok, Solingen (DE); Mark James Form, Wiesbaden-Breckenheim (DE); Arnd Neeff, Burscheid (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/034,512

(22) PCT Filed: Nov. 10, 2014

(86) PCT No.: PCT/EP2014/074174
§ 371 (c)(1),
(2) Date: May 4, 2016

(87) PCT Pub. No.: WO2015/067802
PCT Pub. Date: May 14, 2015

(65) Prior Publication Data
US 2016/0289193 A1    Oct. 6, 2016

(30) Foreign Application Priority Data
Nov. 11, 2013 (EP) ..................................... 13192292

(51) Int. Cl.
C07D 231/12 (2006.01)
C07C 251/88 (2006.01)

(52) U.S. Cl.
CPC .......... *C07D 231/12* (2013.01); *C07C 251/88* (2013.01)

(58) Field of Classification Search
None
See application file for complete search history.

(56) References Cited

U.S. PATENT DOCUMENTS

2013/0197239 A1   8/2013   Pazenok et al.
2014/0228404 A1   8/2014   Hillebrand et al.

FOREIGN PATENT DOCUMENTS

WO   2009106230 A2   9/2009
WO   2013/037768      3/2013

OTHER PUBLICATIONS

Atherton et al. "Cycloaddition Reacthion of 2, 2, 2-Trifluorodiazoethane", Journal of the Chemical Society, Section C:Organic Chemistry, Chemical Society. (1968) pp. 1507-1513.
Pashkevich et al. Zhurnal Vsesoyuznogo Khimicheskogo Obshchestva IM. D.I. Mendeleeva (1981)26(1), pp. 105-107.
International Search Report PCT/EP2014/074174 Mailed Jan. 1, 2015.

*Primary Examiner* — Kamal Saeed
(74) *Attorney, Agent, or Firm* — McBee Moore Woodward Vanik IP LLC

(57) ABSTRACT

The present invention relates to a novel process for preparing 3,5-bis(haloalkyl)pyrazole derivatives.

9 Claims, No Drawings

PROCESS FOR PREPARING 3,5-BIS(HALOALKYL)PYRAZOLE DERIVATIVES FROM A,A-DIHALOAMINES

CROSS REFERENCE TO RELATED APPLICATIONS

This application is a §371 National State Application of PCT/EP2014/074174, filed Nov. 10, 2014, which claims priority to European Application No. 13192292.4 filed Nov. 10, 2014.

BACKGROUND OF THE INVENTION

1. Field of the Invention

The present invention relates to a novel process for preparing 3,5-bis(haloalkyl)pyrazole, especially 3,5-bis(fluoroalkyl)pyrazole derivatives.

2. Description of Related Art

Polyhaloalkylpyrazolylcarboxylic acid derivatives, especially polyfluoroalkylpyrazolylcarboxylic acid derivatives and 3,5-bis(fluoroalkyl)pyrazoles are valuable precursors of active fungicidal ingredients (cf. WO 2003/070705 and WO 2008/013925).

Pyrazolecarboxylic acid derivatives are typically prepared by reacting acrylic acid derivatives having two leaving groups with hydrazines (cf. WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkyl hydrazines.

3,5-Bis(fluoroalkyl)pyrazoles are prepared by reacting bisperfluoroalkyl diketones (e.g. 1,1,1,5,5,5-hexafluoroacetylacetone) with hydrazines (cf. Pashkevich et al., Zhurnal Vsesoyuznogo Khimicheskogo Obshchestva im. D. I. Mendeleeva (1981), 26(1), 105-7), the yield being only 27-40%. The synthesis, isolation and purification of the polyfluoroalkyl diketones is very complex since the compounds are generally very volatile and highly toxic.

SUMMARY

In the light of the prior art described above, it is an object of the present invention to provide a process that does not have the aforementioned disadvantages and hence gives a route to 3,5-bis(haloalkyl)pyrazole, especially 3,5-bis(fluoroalkyl)pyrazole derivatives in high yields.

The object described above was achieved by a process for preparing 3,5-bis(haloalkyl)pyrazoles of the formula (Ia) and (Ib),

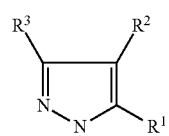
(Ia)

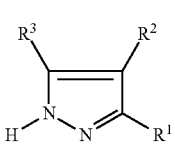
(Ib)

in which $R^1$ and $R^3$ are each independently selected from $C_1$-$C_6$-haloalkyl;

$R^2$ is selected from H, Hal, COOH, (C=O)OR$^4$, CN and (C=O)NR$^4$R$^5$;

$R^4$ and $R^5$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or $R^4$ and $R^5$ together with the nitrogen atom to which they are bonded may form a four-, five- or six-membered ring characterized in that, in step (A), α,α-dihaloamines of the formula (II),

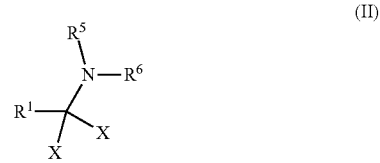
(II)

in which

X is independently selected from F, Cl or Br;

$R^5$ and $R^6$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or $R^5$ and $R^6$ together with the nitrogen atom to which they are bonded may form a five- or six-membered ring;

$R^1$ is as defined above are reacted with compounds of the formula (III),

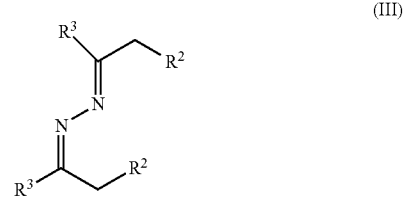
(III)

in which $R^2$ and $R^3$ are as defined above to form the compound of formula (IV) or (V)

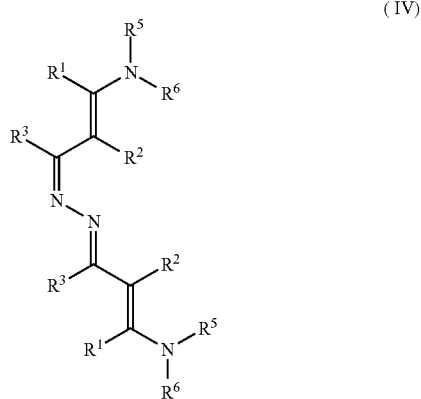
(IV)

-continued

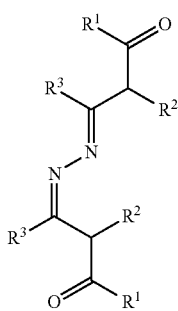

(V)

and that in step (B) in the presence of an acid and hydrazine the cyclization of (IV) or (V) takes place to form (Ia/Ib).

DETAILED DESCRIPTION OF A PREFERRED EMBODIMENT

Preferred is a process according to the invention, where the radicals in formula (Ia), (Ib), (II), (III), (IV) and (V) are defined as follows:
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl and 1,1,1-trifluoroprop-2-yl;
$R^2$ is selected from H, Cl, Br, $COOCH_3$, $COOC_2H_5$, $COOC_3H_7$, CN and $CONMe_2$, CON $(C_2H_5)_2$;
X is independently selected from F or Cl.

Furthermore preferred is a process according to the invention, where the radicals in formula (Ia), (Ib), (II), (III), (IV) and (V) are defined as follows:
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl and 1,1,1-trifluoroprop-2-yl;
$R^2$ is selected from H, Cl, Br, $COOCH_3$, $COOC_2H_5$, $COOC_3H_7$, CN and $CONMe_2$, CON $(C_2H_5)_2$;
X is independently selected from F or Cl;
$R^5$ and $R^6$ are each independently selected from methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl, cyclopropyl, cyclopentyl and cyclohexyl
or
$R^5$ and $R^6$ together with the nitrogen atom to which they are bonded may form a five-membered ring.

More preferred is a process according to the invention, where the radicals in formula (Ia), (Ib), (II), (III), (IV) and (V) are defined as follows are defined as follows:
$R^1$ and $R^3$ are each independently selected from trifluoromethyl, difluoromethyl, difluorochloromethyl, pentafluoroethyl;
$R^2$ is selected from H, Cl, CN, $COOC_2H_5$;
X is independently F or Cl.

Furthermore more preferred is a process according to the invention, where the radicals in formula (Ia), (Ib), (II), (III), (IV) and (V) are defined as follows are defined as follows:
$R^1$ and $R^3$ are each independently selected from trifluoromethyl, difluoromethyl, difluorochloromethyl, pentafluoroethyl;
$R^2$ is selected from H, Cl, CN, $COOC_2H_5$;
X is independently F or Cl;
$R^5$ and $R^6$ are each independently selected from methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl.

Most preferred is a process according to the invention, where the radicals in formula (Ia), (Ib), (II), (III), (IV) and (V) are defined as follows:
$R^1$ and $R^3$ are $CF_2H$;
$R^2$ is selected from H
X is F.

Furthermore most preferred is a process according to the invention, where the radicals in formula (Ia), (Ib), (II), (III), (IV) and (V) are defined as follows:
$R^1$ and $R^3$ are $CF_2H$;
$R^2$ is selected from H;
X is F;
$R^5$ and $R^6$ are methyl.

Surprisingly, the pyrazoles of the formula (I) can be prepared under the conditions according to the invention with good yields and in high purity. That means that the process according to the invention overcomes the above-mentioned disadvantages of the preparation processes previously described in the prior art.

GENERAL DEFINITIONS

In the context of the present invention, the term "halogens" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl ($CF_3$), difluoromethyl ($CHF_2$), $CF_3CH_2$, $CF_2Cl$ or $CF_3CCl_2$.

Alkyl groups in the context of the present invention, unless defined differently, are linear, branched or cyclic saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Alkenyl groups in the context of the present invention, unless defined differently, are linear, branched or cyclic hydrocarbyl groups containing at least one single unsaturation (double bond). The definition $C_2$-$C_{12}$-alkenyl encompasses the widest range defined herein for an alkenyl group. Specifically, this definition encompasses, for example, the meanings of vinyl; allyl (2-propenyl), isopropenyl (1-methylethenyl); but-1-enyl (crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl or penta-1,3-dienyl.

Alkynyl groups in the context of the present invention, unless defined differently, are linear, branched or cyclic hydrocarbyl groups containing at least one double unsaturation (triple bond). The definition $C_2$-$C_{12}$-alkynyl encompasses the widest range defined herein for an alkynyl group. Specifically, this definition encompasses, for example, the meanings of ethynyl (acetylenyl); prop-1-ynyl and prop-2-ynyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 1:

Scheme 1:

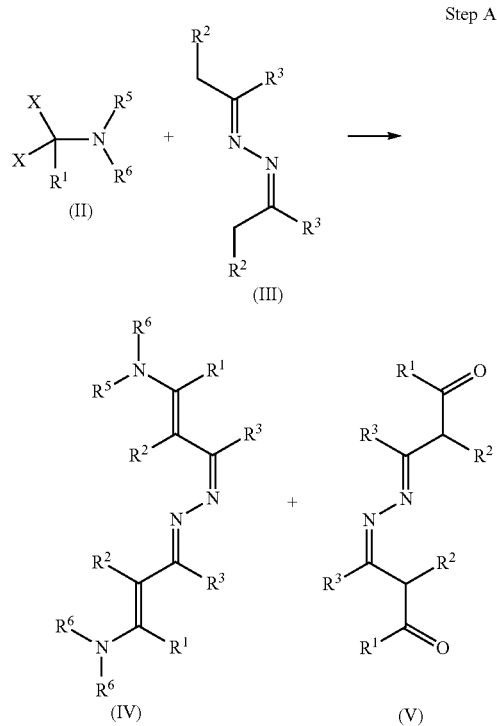

-continued

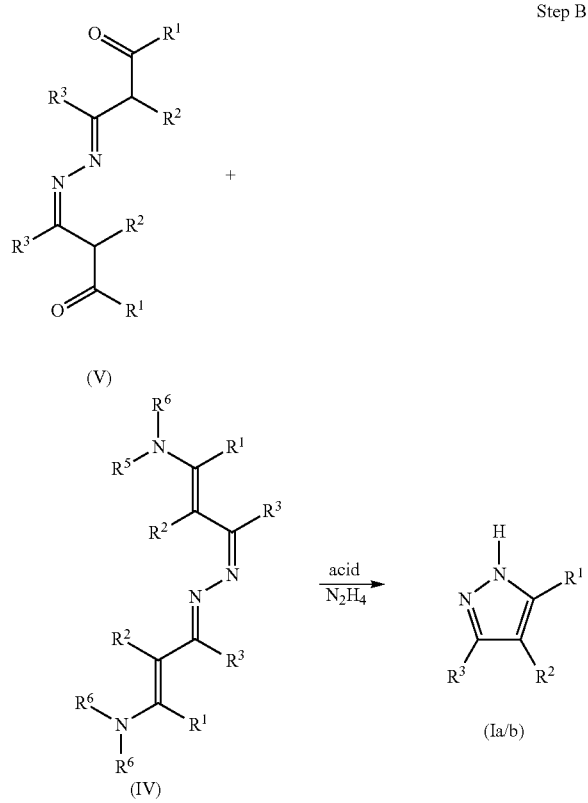

Scheme 2:

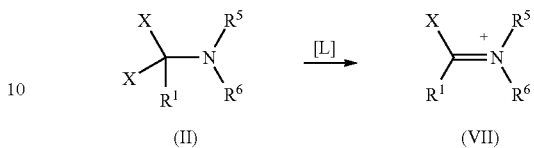

Step (A)

In step (A), α,α-dihaloamines of the formula (II) are first reacted in the presence of a Lewis acid [L], with compounds of the formula (III). In some cases the reaction also works without a Lewis acid [L].

Preferred compounds of the general formula (II) are 1,1,2,2-tetrafluoroethyl-N,N-dimethylamine (TFEDMA), 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N-diethylamine (Ishikawa's reagent), 1,1,2-trifluoro-2-chloroethyl-N,N-dimethylamine and 1,1,2-trifluoro-2-chloroethyl-N,N-diethylamine (Yarovenko's reagent).

Compounds of the general formula (II) are used as aminoalkylating agents. Preference is given to 1,1,2,2-tetrafluoroethyl-N,N-dimethylamine (TFEDMA) and 1,1,2,2-tetrafluoroethyl-N,N-diethylamine, and particular preference to 1,1,2,2-tetrafluoroethyl-N,N-dimethylamine. α,α-Dihaloamines such as TFEDMA and Ishikawa's reagent are commercially available or can be prepared (cf. Yarovenko et al., Zh. Obshch. Khim. 1959, 29, 2159, Chem. Abstr. 1960, 54, 9724h or Petrov et al., J. Fluor. Chem. 109, 2001, 25-31.

Yagupolskii et al. (Zh. Organicheskoi Khim. (1978), 14(12), 2493-6) shows that the reaction of Yarovenko's reagent (FClCHCF$_2$NEt$_2$) with nitriles of the formula RCH$_2$CN (R═CN, CO$_2$Et) affords the derivatives of the formula (NC)RC═C(NEt$_2$)CHFCl in approx. 70% yield. Keto compounds of the formula (III) do not react with α,α-dihaloamines of the formula (II) under this condition.

Petrov et al. (J. of Fluorine Chem. (2011), 132(12), 1198-1206) shows that TFEDMA (HCF$_2$CF$_2$NMe$_2$) reacts with cyclic β-diketones to transfer a difluoroacetyl group.

In a preferred embodiment the α,α-dihaloamine are first reacted with Lewis acid [L], for example BF$_3$, AlCl$_3$, SbCl$_5$, SbF$_5$, ZnCl$_2$, and then compound of the formula (III) is added in substance or dissolved in a suitable solvent (cf. WO 2008/022777).

α,α-Dihaloamines are reacted with Lewis acids [L] (preparation of the iminium salts of the formula (VIII) according to the teaching of WO 2008/022777). According to the invention, the reaction is effected at temperatures of −20° C. to +40 OC, preferably at temperatures of −20° C. to +30 OC, more preferably at −10 to 20° C. and under standard pressure. Due to the hydrolysis sensitivity of the α,α-dihaloamines, the reaction is conducted in an anhydrous apparatus under inert gas atmosphere.

The reaction time is not critical and may, according to the batch size and temperature, be selected within a range between a few minutes and several hours.

According to the invention, 1 mol of the Lewis acid [L] is reacted with equimolar amounts of the α,α-dihaloamine of the formula (II).

For the process according to the invention 1.8 to 4, preferably 2 to 3 mol of the compound of the formula (II) is reacted with 1 mol of azine of the formula (III).

Preference is given to using compounds of the formula (III) selected from the group comprising—bis(1,1,1-trifluoropropan-2-ylidene)hydrazine, bis(1,1-difluor-1-chlorpropan-2-ylidene)hydrazine, bis(1,1-difluoropropan-2-ylidene)hydrazine.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, to acetonitrile, THF, ether or dichloromethane.

The intermediates of the formula (IV) and (V) formed in step A (Scheme 1) can be used in the cyclization step B (Scheme 1) without prior workup.

Alternatively, the intermediates can be isolated and characterized by suitable workup steps and optionally further purification.

Compounds of formula (III) can be prepared according to a procedure described in J. Org. Chem. 1972, 37, 1314-1316:

Scheme 3

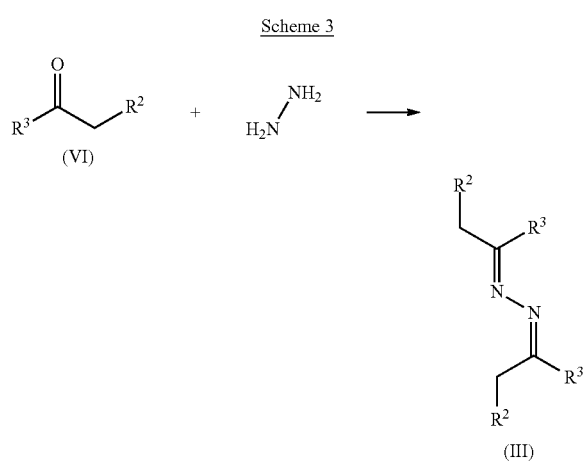

Compounds of formula (VI) which are commercially available are reacted with hydrazine hydrate in the presence of a Lewis Acid, preferably $BF_3$ and $AlCl_3$, and a solvent to form compounds of formula (III). The reaction temperature is $-10°$ C. to $+60°$ C., preferably $0°$ C. to $50°$ C. As solvent can be used alcohols and ethers, preferably ethanol. The ratio of compound of formula (VI) and hydrazine hydrate is 10:1 to 2:1, preferably 5:1 to 2:1 and more preferably 3:1 to 2:1.

Step (B)

The cyclization in step (B) by reaction of compound (IV) or (V) under acidic conditions with hydrazine in the process according to the invention is effected at temperatures of $0°$ C. to $+80$ OC, preferably at temperatures of $+20°$ C. to $+60$ OC, more preferably at $+40$-$50°$ C. and under standard pressure.

The reaction time is not critical and may, according to the batch size, be selected within a relatively wide range.

Typically, the cyclization step (B) is effected without changing the solvent.

Typically the cyclization of compound of the formula (IV) or (V) proceeds under acidic condition.

Preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid.

According to the invention, 0.1 mol to 2 mol, preferably 0.1 to 1.5 mol of the acid for 1 mol of the compound of formula (IV) or (V) is used. According to the invention, the reaction is effected at temperatures of $-20°$ C. to $+80$ OC, preferably at temperatures of $-10°$ C. to $+60$ OC, more preferably at $+10°$ C. to $50°$ C. and under standard pressure. The reaction time is not critical and may, according to the batch size and temperature, be selected within a range between a few minutes and several hours. In most cases it is enough to add just a water to the reaction mixture after step 1 to achieve low pH due the formation of acid (HF) during the step 1.

According to the invention, 1 mol to 2 mol, preferably 1 to 1.5 mol of the hydrazine for 1 mol of the compound of formula (IV) or (V) is used. Hydrazine could be used in the form of its salt like hydrazine hydrochloride or sulphate. According to the invention, the cyclization is effected at temperatures of $-20°$ C. to $+80°$ C., preferably at temperatures of $-10°$ C. to $+60$ OC, more preferably at $+20°$ C. to $50°$ C. and under standard pressure. The reaction time is not critical and may, according to the batch size and temperature, be selected within a range between a few minutes and several hours.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to acetonitrilestoluene, xylene, chlorobenzene, n-hexane, cyclohexane or methylcyclohexane, and very particular preference, for example, to acetonitriles, THF, toluene or xylene. After the reaction has ended, for example, the solvents are removed and the product is isolated by filtration, or the product is first washed with water and extracted, the organic phase is removed and the solvent is removed under reduced pressure.

The compounds of the formula (I) where $R^2$ equals $COOR^4$ can then be converted to pyrazole acids of the formula (I) $R^2$ equals COOH.

The conversion is generally performed under acidic or basic conditions.

For acidic hydrolysis, preference is given to mineral acids, for example $H_2SO_4$, HCl, $HSO_3Cl$, HF, HBr, HI, $H_3PO_4$ or organic acids, for example $CF_3COOH$, p-toluenesulphonic acid, methanesulphonic acid, trifluoromethanesulphonic acid. The reaction can be accelerated by the addition of catalysts, for example $FeCl_3$, $AlCl_3$, $BF_3$, $SbCl_3$, $NaH_2PO_4$. The reaction can likewise be performed without addition of acid, only in water.

Basic hydrolysis is effected in the presence of inorganic bases such as alkali metal hydroxides, for example lithium hydroxide, sodium hydroxide or potassium hydroxide, alkali metal carbonates, for example $Na_2CO_3$, $K_2CO_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, $Na_2CO_3$ or $K_2CO_3$.

Preference is given to conversion by means of basic hydrolysis.

The process step of the invention is performed preferably within a temperature range from $20°$ C. to $+150°$ C., more preferably at temperatures of $30°$ C. to $+110$ OC, most preferably at $30°$ C. to $80°$ C.

The process step of the invention is generally performed under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours.

The reaction step can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides we dimethylformamide (DMF) or N-methylpyrrolidone (NMP) or mixtures of such solvents, particular preference being given to water, acetonitrile, dichloromethane and alcohols (ethanol).

The inventive compounds (Ia) and (Ib) are used for preparation of active fungicidal ingredients.

EXAMPLE 1

Bis(1,1-difluoropropan-2-ylidene) hydrazine (III-1)

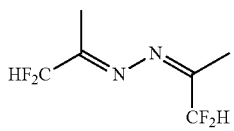

(III-1)

To a stirred solution of difluoroacetone (32 g, 0,342 mmol) in 300 ml methyl-tert.butyl ether hydrazine hydrate (8.6 g., 0, 171 mmol) was added at 0° C. After stirring at room temperature for 1 h the addition product was observed in $^{19}$F-NMR showing two diastereomeres. 0.1 ml of BF$_3$-etherate was added. The mixture was stirred under reflux for 40 min. After drying over Na$_2$SO$_4$ all volatiles were removed and the residue was distilled at 125° C. to 127° C. to give the desired product bis(1,1-difluoropropan-2-ylidene) hydrazine (III-1) as yellow liquid.

Yield: 23 g, 125 mmol, 73%.

EXAMPLE 2

Bis(1,1,1-trifluoropropan-2-ylidene)hydrazine (III-2)

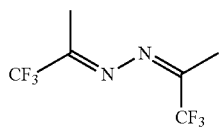

(III-2)

is prepared analogously to the compound of example 1 from trifluoroacetone. b.p.: 58-60° C./180 mbar.

EXAMPLE 3

3,5-bis(difluoromethyl)-1H-pyrazole (I-1)

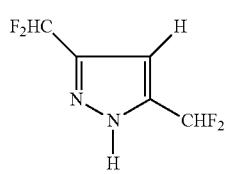

(I-1)

To a solution of TFEDMA (4.35 g, 30 mmol) in 20 mL CH$_3$CN under Argon in a Teflon flask BF$_3$(OEt$_2$) (4.25 g, 30 mmol) was added at 10° C. The solution was stirred for 15 min at room temperature and a solution of (1.84 g., 10 mmol) of bis(1,1-difluoropropan-2-ylidene) hydrazine in 5 ml CH$_3$CN was added and the mixture was stirred at the room temperature for 18 h. After 18 h (1.5 g, 22 mmol) of hydrazin hydrochloride and 5 ml water were added to the reaction mixture. The mixture was stirred for 4 h at 40° C. and the solvent was removed in vacuo at 30° C. The residue was dissolved in 50 ml methyl-tert.butylether and washed 3 times with water. After solvent removal the oil product which slowly solidified was obtained. For further purification the crude product could be distilled in vacuo or purified by column chromatography on silica gel with pentane/diethyl ether (100:0 to 60:40) as eluent to afford the pure title compound (2.72 g, 81%) as a pale yellow solid.

$^1$H NMR (400 MHz, CDCl$_3$) δ 12.5 (br, 1H), 6.77 (t, 2H, J=54.8 Hz), 6.74 (s, 1H); $^{13}$C (101 MHz, CDCl$_3$) δ 142.9, 109.3 (t, J$_{C-F}$=236 Hz), 103.2; $^{19}$F (376 MHz, CDCl$_3$) δ −113.2 (d, 4F, J=54.4 Hz); HRMS (ESI) calc. for C$_5$H$_5$F$_4$N$_2$ [M+H]$^+$ 169.039. found 169.038.

The invention claimed is:

1. A process for preparing a 3,5-bis(haloalkyl)pyrazole of formula (Ia) and (Ib)

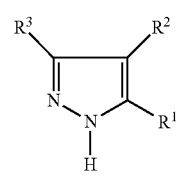

(Ia)

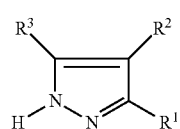

(Ib)

in which

R$^1$ and R$^3$ are each independently selected from C$_1$-C$_6$-haloalkyl;

R$^2$ is selected from H, Hal, COOH, (C=O)OR$^4$, CN and (C=O)NR$^4$R$^5$;

R$^4$ and R$^5$ are each independently selected from C$_{1-12}$-alkyl, C$_{3-8}$-cycloalkyl, C$_{6-18}$-aryl, C$_{7-19}$-arylalkyl and C$_{7-19}$-alkylaryl, or R$^4$ and R$^5$ together with the nitrogen atom to which they are bonded may form a four-, five- or six-membered ring;

comprising in (A), reacting one or more α,α-dihaloamines of the formula (II),

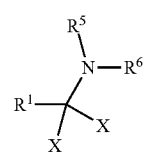

(II)

in which
X is independently selected from F, Cl or Br;
$R^5$ and $R^6$ are each independently selected from $C_{1-12}$-alkyl, $C_{3-8}$-cycloalkyl, $C_{6-18}$-aryl, $C_{7-19}$-arylalkyl and $C_{7-19}$-alkylaryl or where
$R^5$ and $R^6$ together with the nitrogen atom to which they are bonded may form a five- or six-membered ring;
$R^1$ is as defined above;
with one or more compounds of formula (III),

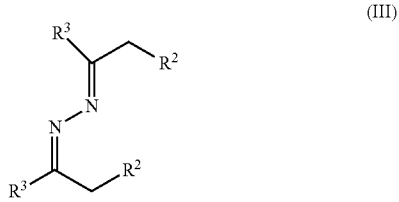

in which
$R^2$ and $R^3$ are as defined above;
to form the compound of formula (IV) or (V)

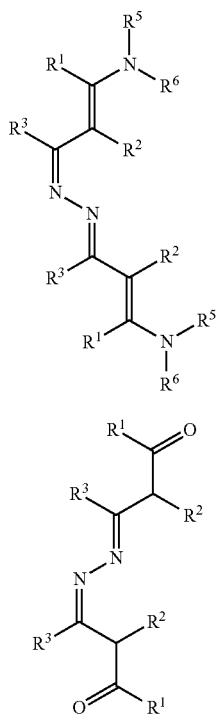

and in (B) in the presence of an acid and hydrazine cyclization of (IV) or (V) takes place to form (Ia/Ib).

2. A process according to claim 1, wherein
$R^1$ and $R^3$ are each independently selected from trifluoromethyl, difluoromethyl, difluorochloromethyl, pentafluoroethyl;
$R^2$ is selected from H, Cl, CN, COOC$_2$H$_5$;
X is independently F or Cl.

3. A process according to claim 1, wherein
$R^1$ and $R^3$ are each independently selected from trifluoromethyl, difluoromethyl, difluorochloromethyl, pentafluoroethyl;
$R^2$ is selected from H, Cl, CN, COOC$_2$H$_5$;
X is independently F or Cl;
$R^5$ and $R^6$ are each independently selected from methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl.

4. A process according to claim 1, wherein
$R^1$ and $R^3$ are CF$_2$H;
$R^2$ is selected from H;
X is F.

5. A process according to claim 1, wherein
$R^1$ and $R^3$ are CF$_2$H;
$R^2$ is selected from H;
X is F;
$R^5$ and $R^6$ are methyl.

6. A process according to claim 1 wherein the compound of formula (II) is 1,1,2,2-tetrafluoroethyl-N,N-dimethylamine (TFEDMA), 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)-ethyl-N,N-diethylamine, 1,1,2-trifluoro-2-chloroethyl-N,N-dimethylamine or 1,1,2-trifluoro-2-chloroethyl-N,N-diethylamine.

7. A compound of formula (III-1): Bis(1,1-difluoropropan-2-ylidene) hydrazine

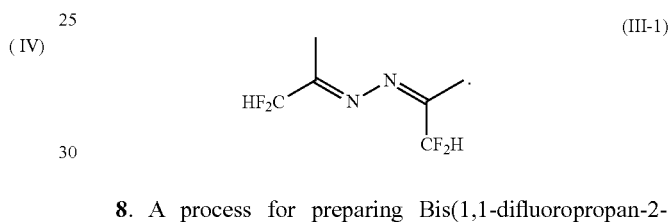

8. A process for preparing Bis(1,1-difluoropropan-2-ylidene) hydrazine of formula (III-1)

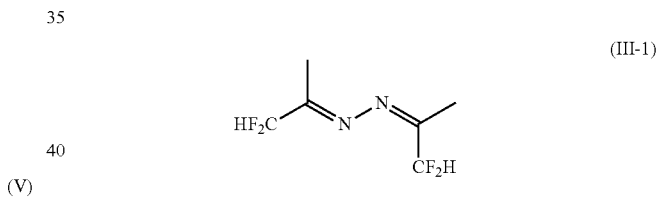

wherein one or more ketones of formula (VI),

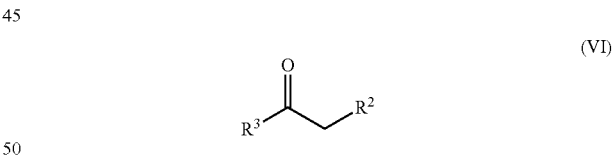

in which
$R^3$ is selected from $C_1$-$C_6$-haloalkyl;
$R^2$ is selected from H, Hal, COOH, (C=O)OR$^4$, CN and (C=O)NR$^4$R$_5$;
$R^4$ and $R^5$ are each independently selected from $C_{1-12}$-alkyl, $C_{3-8}$-cycloalkyl, $C_{6-18}$-aryl, $C_{7-19}$-arylalkyl and $C_{7-19}$-alkylaryl, or
$R^4$ and $R^5$ together with the nitrogen atom to which they are bonded may form a four-, five- or six-membered ring;
are reacted with hydrazine hydrate in the presence of a Lewis Acid and a solvent.

9. The process for preparing Bis(1,1-difluoropropan-2-ylidene) hydrazine of formula (III-1) according to claim 8, wherein the Lewis Acid comprises BF$_3$ or AlCl$_{13}$.

* * * * *